United States Patent [19]
Heil

[11] Patent Number: 5,558,621
[45] Date of Patent: Sep. 24, 1996

[54] SURGICAL RETRACTOR WITH CROSS BAR GRIPS

[75] Inventor: Thomas L. Heil, Pittsburgh, Pa.

[73] Assignee: Heil Associates Inc., Pittsburgh, Pa.

[21] Appl. No.: 426,976

[22] Filed: Apr. 24, 1995

[51] Int. Cl.$^6$ ............................................. A61B 17/02
[52] U.S. Cl. ........................... 600/226; 600/213; 600/201; 16/111 R
[58] Field of Search ........................... 600/213, 226, 600/234, 201, 204, 227; D24/133, 135; 254/133; 16/111 R; 294/57, 58

[56] References Cited

U.S. PATENT DOCUMENTS

| D. 30,951 | 6/1899 | Saint Cyr, Jr. ................. D24/133 |
| D. 69,775 | 3/1926 | Schaeffer ...................... D24/133 |
| 400,589 | 4/1889 | Molesworth ........................ 600/213 |
| 1,601,035 | 7/1925 | Nauth ............................. 600/226 |
| 3,014,750 | 12/1961 | Briggs ............................ 294/58 |
| 3,384,077 | 5/1968 | Gauthier . |
| 3,651,800 | 3/1972 | Wilbanks . |
| 3,729,006 | 4/1973 | Wilder et al. . |
| 3,749,088 | 7/1973 | Kohlmann . |
| 3,965,890 | 6/1976 | Gauthier . |
| 4,151,838 | 5/1979 | Crew . |
| 4,616,633 | 10/1986 | Vargas Garcia . |
| 4,667,657 | 5/1987 | Kulik et al. . |
| 4,767,141 | 8/1988 | Martin ............................. 294/58 |
| 4,836,190 | 6/1989 | Zwick . |
| 4,934,352 | 6/1990 | Sullivan, Jr. . |
| 5,035,232 | 7/1991 | Lutze et al. . |
| 5,080,088 | 1/1992 | LeVahn . |
| 5,232,443 | 8/1993 | Leach . |
| 5,351,679 | 10/1994 | Mayzels et al. ................ 600/226 |
| 5,351,680 | 10/1994 | Jung . |
| 5,363,841 | 11/1994 | Coker . |
| 5,379,758 | 1/1995 | Snyder ............................ 600/213 |
| 5,447,349 | 9/1995 | Coble ............................. 294/58 |

*Primary Examiner*—Richard J. Apley
*Assistant Examiner*—Kelly McGlashen
*Attorney, Agent, or Firm*—Richard C. Litman

[57] ABSTRACT

A handle for a surgical retractor comprises a central, elongated rod member and two gripping and leverage crossbars that intersect the rod member. The handle is useful with a variety of retractor blades for increasing comfort, decreasing fatigue, and improving leverage over a retractor blade.

11 Claims, 1 Drawing Sheet

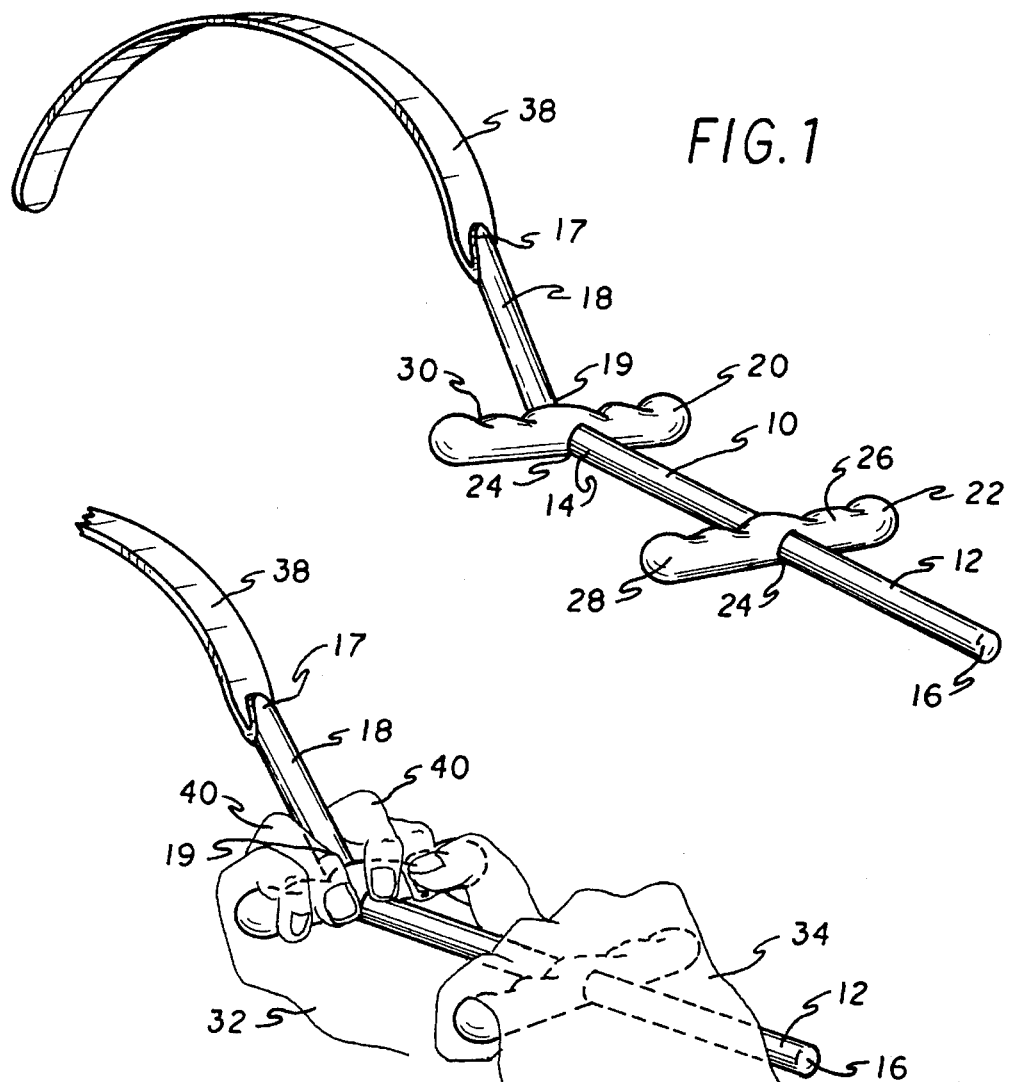
FIG. 1
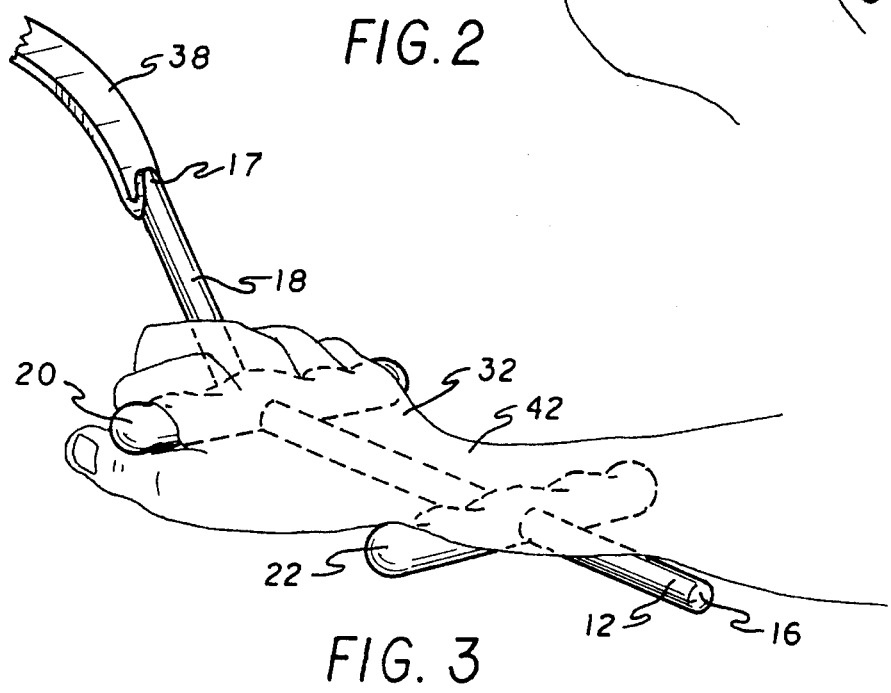
FIG. 2
FIG. 3

5,558,621

SURGICAL RETRACTOR WITH CROSS BAR GRIPS

BACKGROUND OF THE INVENTION

1. Field of the Invention

The present invention relates generally to surgical instruments, and more particularly to handles for surgical retractors.

2. Description of the Prior Art

Surgical retractors are essential implements for many surgical procedures. During the course of surgery, it is frequently necessary to use a retractor to expose tissue that is normally covered by other tissue. Typically, the covering tissue must be held away from the covered tissue during most or all of a surgery, which might last several hours or more. Spending long hours holding an uncomfortable surgical retractor handle is fatiguing, and such fatigue can be dangerous, considering the critical nature of a surgeon's work. Moreover, it is desirable that a handle for a surgical retractor have some structure for providing increased leverage as compared to a standard, stick-like handle. For these reasons, numerous efforts have been made to provide an improved handle for surgical retractors, yet each such effort prior to the present invention has failed in some way to produce a truly comfortable, non-fatiguing handle that simultaneously provides substantial leverage for a user.

U.S. Pat. No. 3,384,077, issued on May 21, 1968, to William K. Gauthier, describes a retractor device with an adjustable blade. The device of this patent is not intended to be held in the hand of a user, and doing so would be rather uncomfortable. This patent does not show use of cross-bars for comfort and leverage.

U.S. Pat. No. 3,651,800, issued on Mar. 28, 1972, to James L. Wilbanks, describes a retractor device with a blade adapted for oral surgery. The device of this patent does not show use of cross-bars for comfort and leverage.

U.S. Pat. No. 3,729,006, issued on Apr. 24, 1973, to Joseph R. Wilder et al., describes disposable retractors having rod-shaped handles without cross-bars for comfort and leverage.

U.S. Pat. No. 3,749,088, issued on Jul. 31, 1973, to William Kohlmann Gauthier, U.S. Pat. No. 3,965,890, issued on Jun. 29, 1976, to William Kohlmann Gauthier, and U.S. Pat. No. 4,010,741, issued on Mar. 8, 1977, to William Kohlmann Gauthier, describe retraction devices having T-shaped handles. The "cross" of the "T" is defined by projections from an end of a central handle member. The central handle member does not extend beyond these projections, and cannot provide the comfort or leverage provided by the present invention.

U.S. Pat. No. 4,151,838, issued on May 1, 1979, to John R. Crew, describes an S-shaped retractor having a perpendicularly-oriented "heel" or cross-bar that serves as a resting place for the retractor when the retractor is used to pry away the sternum during surgery. The cross-bar in this patent is not held in the hand during use of this retractor, and thus does not add to comfort or leverage in use of this retractor.

U.S. Pat. No. 4,616,633, issued on Oct. 14, 1986, to Arturo Vargas Garcia, describes an oral retractor having a curved handle without cross-bars for comfort and leverage.

U.S. Pat. No. 4,667,657, issued on May 26, 1987, to Yaroslav P. Kulik et al., shows a complicated retractor device that is directed to improved retraction itself, rather than to improved holding of a retractor. There are two narrow projections depending from a central handle portion, but the purpose of these projections is not discussed. Because there are only two of these projections and because these projections are relatively narrow, it cannot provide comfort and leverage comparable to that provided by the present invention.

U.S. Pat. No. 4,836,190, issued on Jun. 6, 1989, to Christian R. Zwick, describes a visceral retractor having a terminal extension that acts as a brace against the arm of a user. While this extension provides additional leverage to a user of the retractor, it does so in a way that prevents adjustment of arm position without affecting position of an attached retractor blade. For this reason, this retractor would likely decrease, rather than increase, comfort during use as compared to retractors having conventional handles.

U.S. Pat. No. 4,934,352, issued on Jun. 19, 1990, to Eugene M. Sullivan, Jr., describes a construction for a retractor handle. The construction is such that a terminal portion can be adjusted from an angle of one-hundred-eighty degrees to an angle of ninety degrees, relative to the rest of the handle. In this way, the position of a user's hand can be varied according to the use of the retractor at a particular time. However, making such adjustment during the course of serious surgery would necessitate loss of valuable time, and the retractor of this patent cannot be configured to provide multiple hand-holds simultaneously. For this reason, this patent does not satisfactorily increase leverage or comfort to a user.

U.S. Pat. No. 5,035,232, issued on Jul. 30, 1991, to Theodor Lutze et al., describes a retractor with a handle having a terminal hook-shaped member. This hook-shaped member projects from only one side of the handle, and thus cannot provide the same level of leverage and comfort as the present invention.

U.S. Pat. No. 5,080,088, issued on Jan. 14, 1992, to Bruce A. LeVahn, describes a flexible retraction blade and shows a two-membered handle portion. There are no cross-bars on the handle portion for increasing comfort and leverage.

U.S. Pat. No. 5,232,443, issued on Aug. 3, 1993, to Gary E. Leach, describes a urological retractor with a mechanism for inserting a catheter. There is a central portion with a single, perpendicularly oriented handle. With only one such handle, the handle of this patent cannot provide comfort and leverage comparable to that provided by the present invention.

U.S. Pat. No. 5,351,680, issued on Oct. 4, 1994, to Hong I. Jung, describes a surgical retractor having a curved handle member without cross-bars for comfort and leverage.

U.S. Pat. No. 5,363,841, issued on Nov. 15, 1994, to Wesley L. Coker, describes a retractor for spinal surgery. This retractor has a plurality of specially adapted retractor blade members. The blades are connected to an angle arm that has two laterally disposed studs, oriented perpendicularly to the angle arm. These studs are not meant to be held in the hand, but are instead designed to be inserted by threading into a supporting arm connected to a gear mechanism. This patent does not show cross-bars useful for providing comfort or leverage to a user of a retractor.

None of the above inventions and patents, taken either singly or in combination, is seen to describe the instant invention as claimed.

SUMMARY OF THE INVENTION

A handle for a surgical retractor comprises a central, elongated rod member and two gripping and leverage crossbars through which the rod member extends in a perpendicular orientation to the cross-bars. The handle also has a connector portion that connects the handle to any of a variety of retractor blades. The configuration of the cross-bars relative to the rod member provides a user with several advantages over other handle designs, including increased comfort, reduced fatigue, increased leverage for exposing organs and other tissue during surgery, and simultaneous availability of a variety of holding positions.

Accordingly, it is a principal object of the invention to prevent fatigue of a user of a retractor.

It is another object of the invention to increase a user's leverage over a retraction blade by providing an improved handle for retractor blades, having both a gripping member and a leverage member.

It is a further object of the invention to increase comfort to a user of a retractor during surgery.

Still another object of the invention is to provide a multiplicity of gripping modalities without requiring adjustment of a retractor's configuration.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is an environmental, perspective view of the retractor handle of the present invention shown with a typical retractor blade.

FIG. 2 is an environmental, perspective view of the retractor handle of the present invention showing an exemplary hand-hold, along with part of an illustrative partial retractor blade.

FIG. 3 is an environmental, perspective view of the retractor handle of the present invention showing another exemplary hand hold, along with part of an illustrative partial retractor blade.

Similar reference characters denote corresponding features consistently throughout the attached drawings.

DETAILED DESCRIPTION OF THE PREFERRED EMBODIMENTS

The present invention is a handle for a surgical retractor. The handle provides improved gripping characteristics that increase a user's comfort, decrease fatigue, and improve a user's leverage over a retractor blade connected to the handle. At the same time, the handle allows for a variety of holding modalities, without requiring adjustment of the handle for each particular modality. In these ways, the handle is substantially more useful than handles on conventional retractors, in the very situations in which conventional retractors are typically used. For example, surgical retractors are frequently used in abdominal surgeries during which great tissue masses must be pulled away from their normal position for extended periods of time. It is during this process of exposure that functionality of a retractor's handle becomes critical. Forcing tissue apart for any extended period of time can require an exhausting effort with a conventional retractor handle, so the present invention has structure that adds leverage over the retractor blade. Even with leverage-providing structure in a retractor, holding such a retractor handle in an appropriate position can be fatiguing, unless it is possible to adjust one's hands periodically, without concomitantly moving the retractor blade to an inappropriate position. The present invention provides desirable leverage while allowing gripping of a retractor handle using a variety of hand positions.

Referring to the drawings, the surgical retractor handle 10 of the present invention comprises a central, elongated rod member 12 having a forward end 14, and a rear end 16, a connector portion 18, and two gripping and leverage crossbars 20, 22 with which the rod member 12 intersects, preferably by passing through an aperture 24 in each crossbar.

Preferably, the gripping and leverage crossbars 20, 22 are elongated, cylindrical, one-piece bars having a centrally located aperture 24 of a size such that the rod member 12 can pass through the aperture 24, at right angles to the crossbars 20, 22. It is also preferable that the crossbars 20, 22 and the rod member 12 lie in a single geometrical plane. Alternately, the crossbars 20, 22 could be of a variety of shapes, or could be bi-partite, with one part 26 projecting from one side of the rod member at one angle, while a second part 28 projects from another side of the rod member 12 in another direction (not shown). Regardless of the shape and orientation of the crossbars 20, 22, it is desirable that hill-and-valley style indentations 30 be disposed along the crossbars 20, 22, in order to improve the gripping function of the crossbars 20, 22 in a user's hands. The crossbars 20, 22 are preferably disposed on the rod member 12 so that a forward crossbar 20 is disposed adjacent to a rear end 19 of the connector 18 to the forward end 14 of the rod member 12, and a rear crossbar 22 is disposed intermediate, preferably mid-way, between the forward crossbar 20 and a rearward end 16 of the rod member 12. Other distance relationships between the crossbars 20, 22 and the ends 14, 16 of the rod member 12 could be employed. Preferably, the crossbars 20, 22 are at least as long as a typical user's hands 32, 34 are wide, as shown in FIGS. 2 and 3. In this way, advantages of the handle 10, such as leverage and comfort, are retained regardless of the overall size of the handle 10.

FIG. 2 shows a sample hand position, in which two hands 32, 34 are depicted in a comfortable, high-leverage orientation. FIG. 3 shows another hand position, in which a single hand 32 can both grip the handle 10 and also provide leverage to an attached blade 38, with comfort and ease. Fingers of a user's hand 32 are disposed along on a forward crossbar 20, with fingers 40 on each side of the rod member 12. With the hand 32 in this position, the wrist 42 or lower arm can provide leverage on the handle, and hence on an attached retractor blade 38, by applying pressure to a rear crossbar 22. Many other hand orientations are possible, and would depend on particular preferences of a user of the handle, as well as particular circumstances in which the handle is used.

The connector portion 18, having a front or distal end 17 and the rear or proximal end 19, depends from the rod member 12 at an angle of between one hundred five and one hundred eighty degrees, and preferably at an angle of about one hundred sixty degrees. For the sake of clarity, depending from the rod member 12 at an angle of one hundred eighty degrees refers to a connector portion 18 that is on the very same axis as the rod member 12; whereas, depending from the rod member 12 at an angle of less than ninety degrees would refer to a connector portion 18 that angles back toward the rod member 12.

The handle 10 can be used with a variety of retractor blades, such as blades known as Harrington, Dever, Richardson, Foss, and Ribbon or Malleable. Such blades are attached by known means to the front end 17 of the connector portion 18. These means for attachment, include, but are not limited to, welding, adhesives, and bolting means. The handle 10 can be constructed of a variety of materials, such as surgical steel. Moreover, the handle 10 can be manufactured to a variety of dimensions, depending on the particular way in which the combination of the retractor handle 10 and blade 38 will be employed. For example, if large amounts of tissue must be exposed, a larger handle 10 would be appropriate; whereas, if less tissue is involved or there is less room for maneuvering the handle 10, a smaller handle 10 would be appropriate.

It is to be understood that the present invention is not limited to the embodiments described above, but encompasses any and all embodiments within the scope of the following claims.

I claim:

1. A surgical retractor comprising
   a retractor blade; and
   a handle including,
      an elongated central rod member having a front end and a rear end,
      a connector portion having a distal end and a proximal ends, said connector portion attached at said distal end to said retractor blade, said connector portion attached at said proximal end to said front end of said rod member,
      a first gripping and leverage crossbar attached to said rod member proximate said front end, and
      a second gripping and leverage crossbar attached to said rod member intermediate between said front end and said rear end.

2. The surgical retractor according to claim 1, wherein:
   said crossbars each have a central aperture; and
   said rod member passes through each said crossbars at said central aperture of each of said crossbars.

3. The surgical retractor according to claim 1, wherein said crossbars are configured in a perpendicular orientation to said central rod member.

4. The surgical retractor according to claim 1, wherein said crossbars lie in a single geometric plane.

5. The surgical retractor according to claim 1, wherein said crossbars have hill-and-valley indentations.

6. The surgical retractor according to claim 1, wherein said connector portion depends from said rod member at an angle of between one hundred five and one hundred eighty degrees.

7. The surgical retractor according to claim 6, wherein said connector portion depends from said rod member at an angle of about one hundred sixty degrees.

8. A surgical retractor comprising:
   a retractor blade; and
   a handle including,
      an elongated central rod member having a front end and a rear end,
      a connector portion having a distal end and a proximal end, said connector portion attached at said distal end to said retractor blade, said connector portion attached at said proximal end to said front end of said rod member,
      a first bi-partite crossbar attached to said central rod member proximate said front end of said central rod member; and
      a second bi-partite crossbar attached to said central rod member intermediate between said front end and said rear end.

9. The surgical retractor according to claim 8, wherein said crossbars have hill-and-valley indentations.

10. The surgical retractor according to claim 8, wherein said connector portion depends from said rod member at an angle of between one hundred five and one hundred eighty degrees.

11. The surgical retractor according to claim 10, wherein said connector portion depends from said rod member at an angle of about one hundred sixty degrees.

* * * * *